United States Patent
Maulide et al.

(10) Patent No.: US 9,388,182 B2
(45) Date of Patent: Jul. 12, 2016

(54) PROCESS FOR CONVERTING LUPANINE INTO SPARTEINE

(71) Applicant: STUDIENGESELLSCHAFT KOHLE MBH, Mülheim an der Ruhr (DE)

(72) Inventors: Nuno Maulide, Vienna (AT); Bo Peng, Urbana, IL (US); Carlos Alberto Mateus Afonso, Sobreda (PT); Raquel Frutuoso Machado Frade, Lisbon (PT)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days.

(21) Appl. No.: 14/894,064

(22) PCT Filed: May 20, 2014

(86) PCT No.: PCT/EP2014/060372
§ 371 (c)(1),
(2) Date: Nov. 25, 2015

(87) PCT Pub. No.: WO2014/191261
PCT Pub. Date: Dec. 4, 2014

(65) Prior Publication Data
US 2016/0096840 A1    Apr. 7, 2016

(30) Foreign Application Priority Data
May 28, 2013   (EP) .................................... 13169588

(51) Int. Cl.
*C07D 471/22*   (2006.01)
(52) U.S. Cl.
CPC .................................... *C07D 471/22* (2013.01)
(58) Field of Classification Search
USPC ............................................................ 546/63
See application file for complete search history.

(56) References Cited

PUBLICATIONS

Przybyl, Anna K. et al: "Simple and highly efficient preparation and characterization of (−)-", Tetrahedron, vol. 67, No. 40, 2011, pp. 7787-7793, XP002722212.
Goldberg, Stanley I. et al: "The Structure of Nuttalline, an Alkaloid Constituent of Lupinus nuttallii", Journal of the Chemical Society [Section] D: Chemical Communications, vol. 12, Jan. 1, 1969.
Golebiewski, W. Marek et al: "Lactams of sparteine"., Canadian Journal of Chemistry, vol. 63, No. 3, 1985, pp. 716-719.
Ebner, Thomas et al: "2,3-Didehydrosparteine", Liebigs Annalen Der Chemie, No. 2, 1989, pp. 197-201.
Ebner, Thomas et al: "Über die stereospezifische Hydroxylierung von (+)-Spartein (Pachycarpin) bei der Ratte", Archiv Der Pharmazie, vol. 322, No. 7, 1989, pp. 399-403.
International Search Report from corresponding application PCT/EP2014/060372 mailed Jul. 29, 2014.

*Primary Examiner* — Charanjit Aulakh
(74) *Attorney, Agent, or Firm* — Norris McLaughlin & Marcus, P.A.

(57) ABSTRACT

The present invention relates to processes for preparing enantiopure Lupanine and Sparteine.

15 Claims, No Drawings

PROCESS FOR CONVERTING LUPANINE INTO SPARTEINE

This application is a 371 of PCT/EP2014/060372, filed May 20, 2014, which claims foreign priority benefit under 35 U.S.C. §119 of the European Patent Application No. 13169588.4 filed May 28, 2013, the disclosures of which are incorporated herein by reference.

The present invention relates to a process for preparing enantiopure Lupanine and Sparteine in high yields.

Lupanine and Sparteine, two prominent members of the tetracyclic quinolizidine alkaloid family, are important pharmaceutical compounds and enjoy considerable popularity in synthesis. For instance, Lupanine can be used as a hyperglycemia agent or as starting material for synthesis of other alkaloids. L-(−)-Sparteine is widely employed as ligand or promoter for various asymmetric reactions due to its unique chiral diamine backbone.

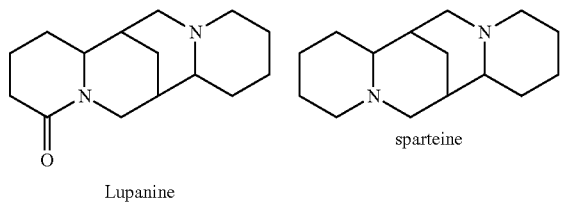

Lupanine                                     sparteine

Commercially available rac-Lupanine is normally isolated from the seeds of *Lupinus albus* while available L-(−)-Sparteine stems from *Cytisus scoparius*. The extraction of quinolizidine alkaloids from plants is a practice dating back to the 1930's and several different methods exist. Typically, dried plants were extracted with alcohol and additional extractions of the resultant residue were made with water prior to addition of sodium hydroxide and final extraction with chloroform.

More recently, quinolizidine alkaloids have been extracted by an extraction of the freeze-dried plant material in 5% (w/v) trichloroacetic acid and successive basifications of the supernatant followed by extractions with dichloromethane. Root lupin extracts have also been produced with 80% aqueous methanol and alkaloids have been separated by retention in a modified silica gel column: Lupanine and 13-hydroxy-Lupanine were obtained with a recovery of 84% and 65%, respectively. Surprisingly, isolation of individual lupin alkaloids has not been explored significantly. As far as isolation of Lupanine is concerned, the known procedures generally consume very large amounts of solvents (petroleum ether—2000 mL/100 g seeds; diethyl ether—2000 mL/g seeds; dichloromethane—2000 mL/100 g seeds) or require a pretreatment of the seeds. DE 44 18 618 C1, for example, discloses a process for obtaining lupine alkaloids from finely ground *Lupine albus* seeds The development of straightforward and environmentally friendly methodologies to extract and isolate Lupanine from *Lupine albus* seeds should be a valuable endeavour, especially given the natural abundance and ease of access to this species.

Similarly, the preparation of optically pure Lupanine and, in particular, the unnatural enantiomer D-(+) of Sparteine has scarcely been reported.

Though asymmetric total syntheses of Sparteine have been achieved, the multistep nature of these approaches ultimately places them far from practical applications.

In the state of art, only two reports have demonstrated the resolution of Lupanine with a chiral acid.

In the earliest example, Clemo et. al. (J. Chem. Soc. 1931, 429-437) demonstrated the resolution of Lupanine with a chiral acid. It was shown that resolution employing L-camphorsulphonic acid and D-camphorsulphonic acid provided L-(−)-Lupanine and D-(+)-Lupanine in 9.4% and 13% yields, respectively, and further reduction of enantiopure Lupanine with red phosphorus afforded either D-(+)-Sparteine or L-(−)-Sparteine.

More recently, Przybyl et al. (Tetrahedron 2011, 67, 7787-7793) improved this resolution process significantly by using dibenzoyltartaric acid and the nontoxic reductant $LiAlH_4$. However, this resolution process involves significant solvent manipulation operations and mandates the use of a large amount of $LiAlH_4$ (8.0 eq) as reducing agent, resulting in serious safety and post-reactional-treatment issues. It is therefore highly desirable to develop more economical and practical processes to access enantiopure Lupanine and Sparteine.

The subject matter of the present invention is a process for a facile and efficient extraction, isolation and chiral resolution of rac-Lupanine into both enantiomers and the conversion thereof by reduction to Sparteine.

The inventors surprisingly found that a simple treatment of raw lupine seeds in alkaline solution at a pH of more than 12, followed by extraction and treatment with pure enantiomers of simple chiral acid, preferably tartaric acid, achieves pure enantiomers of Lupanine. A subsequent reduction of Lupanine using a reducing agent, preferably $NaBH_4$, leads en route to enantiopure Sparteine. Furthermore, the use of large volumes of organic solvents, particularly halogenated ones is avoided by the present invention.

The inventors have developed a process for extraction of Lupanine out of untreated *Lupinus albus* seeds, comprising the steps of a. heating said *Lupinus albus* seeds in a water bath in a temperature range from 80 to 100° C. for a time of at least 15 h;

b. adding an aqueous alkaline solution to adjust a pH in the combined solution of more than 12;

c. filtering off the solids and extracting Lupanine from the solution obtained with an organic solvent.

Optionally, the obtained Lupanine can be further purified, preferably by column chromatography and elution with an organic solvent:

The process for extraction of Lupanine out of untreated *Lupinus albus* seeds can make use of untreated Lupanine seeds, which means that the Lupanine seeds can be used as such without any further treatment such as milling or cutting before heating in said aqueous solution. Said heating is preferably carried out in water in a temperature range from 80 to 120° C., preferably from 90 to 100° C. for a time of at least 15 h, preferably at least 20 h. Optionally, the solution can also be heated in a closed vessel thus providing the option that the seeds can be treated at a temperature of more than 100° C. at an elevated pressure. After said treatment, the solution obtained in step a. is filtered, preferably through Celite, before performing step b.

In step b, an alkaline solution of an alkali hydroxide such as NaOH, or KOH in water is added in order to adjust a pH of more than 12, preferably more than 13.

In step c, extracting Lupanine from the solution using an organic solvent, preferably diethyl ether, preferably using a volume proportion 1:1 of organic phase/aqueous phase, is carried out.

The obtained Lupanine can be purified, preferably by column chromatography wherein the Lupanine is preferably eluted with an organic solvent or a mixture of organic solvents such as ethyl acetate, ether and a basic amine compound such as triethylamine (TEA), more preferably with ethyl acetate and 5% TEA.

The so obtained Lupanine or commercially available Lupanine can be further treated in a process for separating enantiopure Lupanine from rac-Lupanine comprising the steps of
a. dissolving enantiopure chiral acid or a salt thereof in a solvent,
b. dissolving the isolated rac-Lupanine in a solvent, preferably in EtOH,
c. mixing the solutions obtained in steps a) and b), optionally followed by stirring until a solid is formed,
d. separating the obtained Lupanine-enantiopure chiralic acid salt from the aqueous solution;
e. basifying the obtained Lupanine-enantiopure chiralic acid salt, e.g. by KOH,
f. extracting the enantiopure Lupanine by means of an organic solvent and
g. removing of the solvent.

It has been found that an increased yield of the desired enantiomer can be obtained by adding the dissolved Lupanine to a solution of chiral acid, instead of adding the chiral acid to a solution of Lupanine. The chiral acid may be selected from MTPA (methoxy trifluoromethyl phenyl acetic acid), camphersulfonic acid, tartaric acid and is preferably tartaric acid. Thus, it is preferred if, during the mixing step c, the solution of step b. is added to the solution of step a, and, more preferably, to add the solution obtained in step b) dropwise to the solution obtained in step a) and optionally followed by stirring until a solid is formed. The inventors have found out that the amount of L-tartaric acid to the rac-Lupanine influences the separation into the pure enantiomer.

The results of the inventors show that using 0.75 eq of L-Tartaric acid for the resolution gave the best result furnishing D-(+)-Lupanine in 29% yield with 99.0% ee. Accordingly, the inventive process makes preferably use of a stoichiometric ratio of L-tartaric acid to rac-Lupanine of less than 1.25 equivalents, preferably less than 1.00 and more than 0.5 equivalents. The equivalents used in the specification refer to molar equivalents.

Thus, a process is preferred, wherein adding the dissolved Lupanine to a solution of chiral acid of step c) is performed with ratio of 1.0 to 1.5, preferably 1.0 mol equivalents of Lupanine to 0.5 to 1.0, preferably 0.75 mol equivalents of said chiral organic acid per minute.

In a further embodiment, a recrystallisation step can be introduced to further improve the process. Therefore, an organic solvent is added to the product obtained in step d., before step e. is performed, which reaction mixture is then heated under reflux, followed by cooling down. Preferably, EtOH is used as recrystallisation solvent, which in addition simplifies the procedure by using the same solvent for dissolving the rac-Lupanine and for the step of recrystallisation.

Following the crystallisation step, the solution containing said Lupanine-tartrate salt is basified in order to release the Lupanine. The effect of the concentration of alkali hydroxide, preferably potassium hydroxide, was examined and, as shown in Scheme 1, there is no significant improvement upon employing aqueous KOH solutions more concentrated than 10% (w/v). Accordingly, the inventive process makes preferably use of an aqueous solution of an alkali hydroxide, preferably potassium hydroxide, in a concentration ratio less than 10% (w/v), preferably in the range of 5% to 10% (w/v).

Scheme 1. Hydrolysis of D-lupanine L- tartrate with KOH aq.

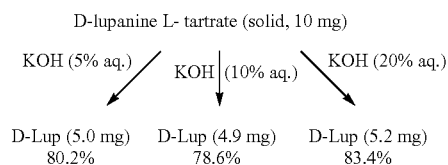

The so-obtained enantiopure Lupanine or any other available Lupanine can be further converted into the desired Sparteine by reducing the carboxy group to a methylene group. From the outset, one of the priorities of the inventors was to avoid the use of $LiAlH_4$ in the reduction of Lupanine to Sparteine. Therefore, the inventors have investigated different systems for this transformation, employing rac-Lupanine for convenience (Scheme 2).

Scheme 2. Reduction of Lupanine with $NaBH_4$

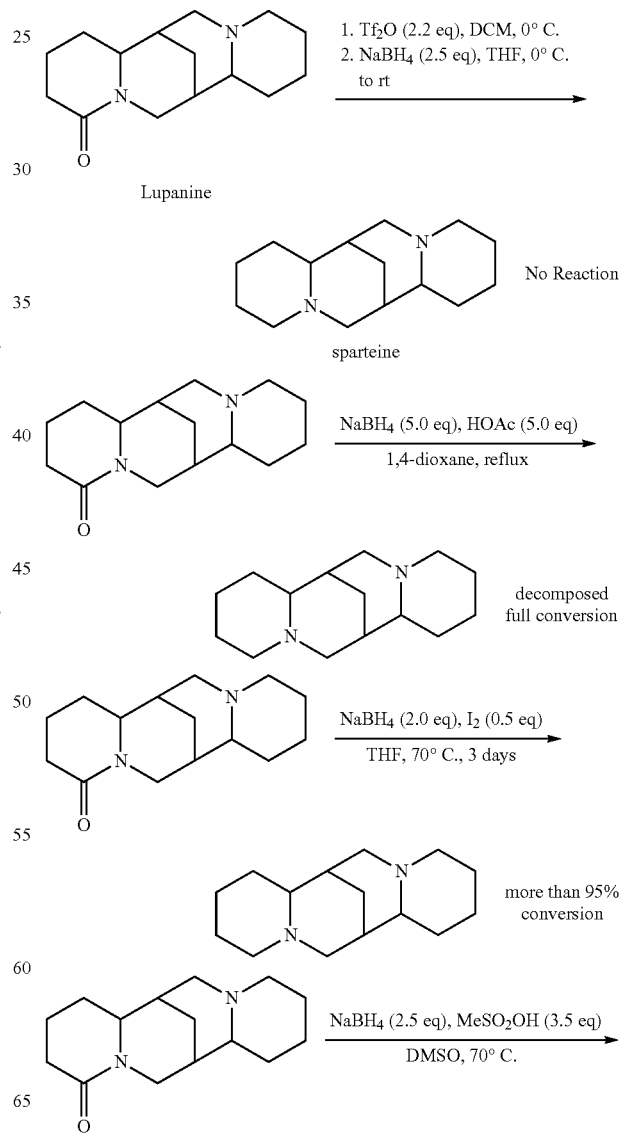

-continued

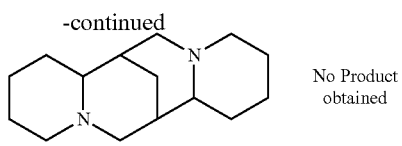

No Product obtained

Surprisingly, the inventors found that the obtained Lupanine enantiomer can be reduced to the corresponding Sparteine by using NaBH$_4$ and I$_2$ in an organic solvent such as THF. Further studies of the inventors on the NaBH$_4$/I$_2$ combination revealed that reducing rac-Lupanine with a ratio of 1.0-4.0 equivalents of NaBH$_4$ and 1.0 eq. of I$_2$ yielded good results, generating rac-Sparteine in a more than 88% isolated yield (Table 2).

TABLE 2

Optimization of NaBH$_4$/I$_2$ system

| entry | NaBH$_4$ | I$_2$ | yield |
|---|---|---|---|
| 1 | 2.0 eq. | 0.5 eq | 90% |
| 2 | 2.0 eq | 0.1 eq | 5% |
| 3 | 1.0 eq | 0.5 eq | 88% |
| 4 | 1.0 eq | 0.1 eq | 5% |

Therefore, the present invention also refers to the process for preparing Sparteine by reducing Lupanine with a combination of NaBH$_4$/I$_2$ more preferably by using a ratio of 1 equivalent iodine to 1-6 equivalent(s). NaBH$_4$, more preferably a 1.5-4.5 equivalents NaBH$_4$, and, most preferred 1.5 to 2.5 equivalents NaBH$_4$, in an organic solvent or a mixture thereof. The solvent can be selected from ethers including diethyl ether, MTBE or cyclic ethers such as dioxane, THF. The reducing agent NaBH$_4$ is preferably used in an at least stoichiometric amount to the Lupanine.

The invention discloses an approach for a simple, more environmentally friendly and reproducible process for the isolation of Lupanine from Lupine albus seeds. It employs smaller volumes of organic solvents (avoiding the use of halogenated solvents such as dichloromethane) than other procedures described in the literature. In the inventive process, the volume of organic solvents was minimized (diethyl ether—600 mL/100 g seeds, and optionally dichloromethane—106 mL/100 g seeds, ethyl acetate—2000 mL/100 g seeds and triethylamine—50 mL/100 g seeds) and the residue obtained after diethyl ether extraction was already of very reasonable purity: 97.1% pure and 1.1% ee of L-(−)-Lupanine by HPLC analysis.

Additionally, a practical and efficient resolution of rac-Lupanine and reduction of enantioenriched Lupanine to Sparteine are described. The resolution procedure uses only cheap and abundant chiral acid such as tartaric acid, affording D-(+)-Lupanine in 29% yield and 99.0% ee and L-(−)-Lupanine in 30% yield and 99.5% ee. Further reduction of the thus obtained, enantiopure Lupanine, using a cheap and convenient NaBH$_4$/I$_2$ system led to L-(−)-Sparteine and D-(+)-Sparteine in good yields. The processes reported herein pave a convenient and cost-effective way to access these two important alkaloids, in particular the unnatural enantiomer of Sparteine.

The invention is further illustrated by the following examples.

Example 1

Extraction of Lupanine

For the extraction, dry Lupinus albus seeds were mixed with water in a flask and heated to 100° C. in a stirring oil bath using an apparatus with a reflux condenser. After 22 hours, the extract was filtered through Celite and the filtered solution was basified (pH=14) with potassium hydroxide (KOH) as alkaline hydroxide. Following basification, extraction of Lupanine was performed with diethyl ether as organic solvent using a proportion 1:1 of organic phase/aqueous phase. The organic phase was dried with anhydrous sodium sulphate and the solvent was removed under reduced pressure. The dried extract was dissolved in dichloromethane as organic solvent and mixed with silica gel. Solvent was carefully evaporated, the thus obtained impregnated silica was placed on top of fresh silica gel in a separating funnel and pure Lupanine was eluted ethyl acetate and a basic organic amine such as 5% triethylamine (TEA) and subsequently dried under vacuum. The amount of Lupanine obtained was 305 mg per 50 grams of lupine dry seeds.

Example 2

Resolution Study

Example 2.1

Resolution Reagent

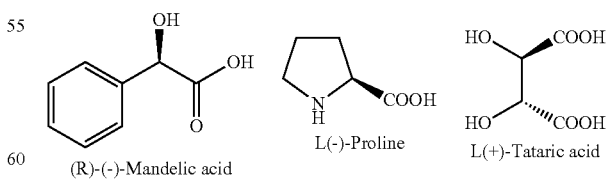

(R)-(−)-Mandelic acid    L-(−)-Proline    L(+)-Tataric acid

At first, different chiral acids were examined for the Lupanine resolution. For instance, a solution of rac-Lupanine (100 mg) in an organic solvent, preferably acetone (1 mL) was added dropwise to a solution of chiral acid such as (R)-(−)-mandelic acid (1.0 eq), L-proline (1.0 eq) or L-tartaric acid (0.5 eq) in (organic solvent, preferably acetone (2 mL). It was found that a white solid formed as soon as L-Tartaric acid was added. Then, the obtained white solid was basified with KOH (5% aq.) as alkaline hydroxide to provide D-(+)-Lupanine with 88.6% ee. When using (R)-(−)-mandelic acid or L-proline, no solid was observed even after prolonged stirring (up to 12 hours) and/or removing acetone. Thus, Tartaric acid was chosen for further studies.

Example 2.2

Order of Addition

In an experiment contrasting with the previous addition sequence, a solution of L-tartaric acid (0.5 eq) in acetone (2 mL) as organic solvent was added to a solution of rac-Lupanine (100 mg) in acetone (1 mL) as organic solvent, also leading to the formation of a white solid. Nevertheless, hydrolysis of this as before gave D-(+)-Lupanine with only 56.0% ee, thus validating the previous addition sequence as superior.

Example 2.3

Recrystallisation Solvent

To improve the resolution process, further recrystallisation of the D-(+)-Lupanine salt was carried out in different solvents such as EtOH, iPrOH, EtOAc, Acetone or MTBE. It was found that D-(+)-Lupanine salt was only soluble in EtOH and the recrystallisation afforded D-(+)-Lupanine-L-tartrate, which could be neutralized with KOH (5% aq.) as alkaline hydroxide to give D-(+)-Lupanine in 19% yield with 99.7% ee.

Example 2.4

Simplified Procedure: Using the Same Solvent for the Resolution and Recrystallisation Steps To further simplify the resolution procedure, EtOH (1 mL) was used instead of acetone to dissolve L-tartaric acid (0.5 eq) in the formation of D-(+)-Lupanine-L-tartrate. Then, recrystallisation of the obtained solid with extra EtOH (2 mL) and hydrolysis gave D-(+)-Lupanine in 16% yield with 99.2% ee.

Example 2.5

D-(+)-Lupanine L-Tartrate Salt

The amount of L-Tartaric acid was investigated as shown in Table 1. The results show that using 0.75 eq of L-Tartaric acid for the resolution gave the best result furnishing D-(+)-Lupanine in 29% yield with 99.0% ee.

TABLE 1 optimization of amount of L-tartaric acid

| entry | amount of L-tartaric acid | yield % | ee % |
| --- | --- | --- | --- |
| 1 | 0.75 eq. | 29% | 99.0% |
| 2 | 1.0 eq. | 30% | 98.9% |
| 3 | 1.25 eq. | 21% | 98.0% |
| 4 | 1.5 eq. | 16% | 97.0% |

To a solution of L-tartaric acid (90.6 mg, 0.75 eq) in EtOH (1 mL) was added a solution of rac-Lupanine (200 mg) in EtOH (1 mL) dropwise over a period of 15 min. After stirring for 2 hours, a solid is formed in the flask and additional EtOH (2 mL) was added to the mixture for further recrystallisation under reflux. Then the mixture was cooled to room temperature and left to stand overnight. Removing solvent by filtration and washing with EtOH (1 mL) led to D-(+)-Lupanine L-tartrate salt as white powder (75 mg) and the recovered mother liquor was kept for further resolution of L-(−)-Lupanine.

Example 3

Preparation of the Enantiomers

Example 3.1

D-(+)-Lupanine

The obtained D-(+)-Lupanine L-tartrate salt (75 mg) was added to 10 mL of KOH (5% aq.) as alkaline hydroxide. The aqueous phase was then extracted with $Et_2O$ (10 mL×5) as organic solvent. The combined organic phases were dried over $Na_2SO_4$ and the solvents were removed, affording D-(+)-Lupanine as a colorless oil (58.0 mg, 29% yield and 99.0% ee).

Example 3.2

L-(−)-Lupanine

L-(−)-Lupanine D-Tartrate Salt
The recovered mother liquor from the preparation of D-(+)-Lupanine L-tartrate salt was concentrated, treated with 10 mL of KOH (5% aq.) as alkaline hydroxide and then extracted $Et_2O$ (10 mL×5) as organic solvent. The combined organic phases were dried over $Na_2SO_4$ and the solvents were removed, affording a crude oil (120 mg, 54% ee). To a solution of the obtained crude oil in EtOH (1 mL) as alcohol solvent was added D-tartaric acid (57 mg, 0.78 eq.). After stirring overnight, white crystals formed in the mixture were recrystallised with addition of more alcohol solvent EtOH (3 mL) under reflux. The mixture was then cooled to room temperature and left to stand overnight. Removing solvent by filtration and washing with the alcohol solvent EtOH (1 mL) resulted in L-(−)-Lupanine D-tartrate salt as white powder (94 mg).
L-(−)-Lupanine:
The obtained L-(−)-Lupanine D-tartrate salt (94 mg) was added to 10 mL of KOH (5% aq.) as alkaline hydroxide. The obtained aqueous phase was extracted with $Et_2O$ (5×10 mL) as organic solvent. The combined organic phases were dried over $Na_2SO_4$ and the solvents were removed, providing L-(−)-Lupanine as a colorless oil (60.0 mg, 30% yield and −99.5% ee).

Example 4

To a solution of Lupanine (49.6 mg) in THF (3 mL) as ether was added $NaBH_4$ (7.6 mg, 1.0 eq) and $I_2$ (25.4 mg, 0.5 eq). The mixture was stirred at 80° C. for 16 hours and then cooled to room temperature. As alcohol MeOH (10 mL) was added and the mixture was subsequently poured into 50 mL of 5% aqueous alkaline hydroxide KOH. The resulting solution was extracted with $Et_2O$ (5×40 mL) as organic solvent, the organic extracts were dried over $Na_2SO_4$ and then concentrated to afford Sparteine as a colorless oil (41.2 mg, 88% yield).

The invention claimed is:

1. A process for converting Lupanine into sparteine, said process comprising the step of treating said Lupanine with a reduction agent, wherein said reduction agent comprises $NaBH_4$ in combination with Iodine, wherein said reduction agent has a ratio of 1 molar equivalent iodine to 1-6 molar equivalent(s) $NaBH_4$, and wherein said Lupanine is treated with said reduction agent in an organic solvent or a mixture of organic solvents.

2. Process according to claim 1, wherein said Lupanine is treated with said reduction agent in a ratio of 1 molar equivalent iodine to 1.5-4.5 molar equivalents $NaBH_4$.

3. Process according to claim 1, wherein said Lupanine is treated with said reduction agent having a ratio of 1 molar equivalent iodine to 1.5 to 2.5 molar equivalents $NaBH_4$.

4. Process as claimed in claim 1, wherein the Lupanine is enantiopure.

5. Process as claimed in claim 1, wherein the Lupanine is racemic.

6. Process as claimed in claim 5, wherein the Lupanine is obtained by a process comprising the steps of:
   a. heating untreated *Lupinus albus* seeds in a water bath in a temperature range from 80 to 120° C. for a time of at least 15 h to form a first solution;
   b. adding an aqueous alkaline solution to the first solution to form a second solution and to adjust a pH in the second solution of more than 12;
   c. filtering off the solids to form a third solution and extracting Lupanine from the third solution with an organic solvent; and optionally
   d. purifying the obtained Lupanine.

7. Process according to claim 6, wherein the extract obtained in step a. is filtered before performing step b.

8. Process according to claim 6, wherein the extraction in step c. is performed with an organic solvent using a proportion 1:1 of organic phase/aqueous phase, and optionally with diethyl ether as organic solvent.

9. Process according to claim 6, wherein in step d. the Lupanine is eluted with an organic solvent, optionally with a content of up to 10% (v/v) of an amine.

10. Process as claimed in claim 4, wherein the Lupanine is obtainable by a process comprising the steps of:
    a. dissolving an enantiopure chiral acid or a salt thereof in a solvent to form a first solution,
    b. dissolving rac-Lupanine in an organic solvent to form a second solution,
    c. mixing the first and second solutions to form a third solution, optionally followed by stirring until a solid precipitate of Lupanine-enantiopure chiral acid salt is formed,
    d. separating the precipitated Lupanine-enantiopure chiral acid salt from the third solution,
    e. basifying the obtained Lupanine-enantiopure chiral acid salt in an aqueous solution,
    f. extracting the enantiopure Lupanine by means of an organic solvent, selected from $Et_2O$, MTBE, and EtOAc, and
    g. removing the solvent.

11. Process according to claim 10, wherein the solvent of step b) is EtOH.

12. Process according to claim 10, wherein in step c, mixing the first and second solutions is achieved by adding the dissolved Lupanine to a solution of the chiral acid.

13. Process according to claim 12, wherein adding the dissolved Lupanine to a solution of chiral acid of step c) is performed with ratio of 1.0 to 1.5 mol equivalents of Lupanine to 0.5 to 1.0 mol equivalents of said chiral organic acid per minute.

14. Process according to claim 10, further comprising a recrystallisation step after step d. before step e., wherein the obtained Lupanine chiral acid salt is recrystallised in an organic solvent.

15. Process according to claim 10, wherein the chiral acid is selected from MTPA, camphersulfonic acid and tartaric acid.

* * * * *